United States Patent
Gesche et al.

(10) Patent No.: US 11,058,777 B2
(45) Date of Patent: Jul. 13, 2021

(54) TUMOR MARKER FOR THE RHABDOMYOSARCOMA

(71) Applicants: Eberhard Karls Universität Tuebingen Medizinische Fakultaet, Tuebingen (DE); DEUTSCHES KREBSFORSCHUNGSZENTRUM STIFTUNG DES OEFFENTLICHEN RECHTS, Heidelberg (DE)

(72) Inventors: Jens Gesche, Tuebingen (DE); Sorin Armeanu-Ebinger, Tuebingen (DE); Guido Seitz, Ammerbuch (DE); Harald Surowy, Heidelberg (DE)

(73) Assignees: EBERHARD KARLS UNIVERSITÄT TUEBINGEN MEDIZINISCHE FAKULTAET, Tuebingen (DE); DEUTSCHES KREBSFORSCHUNGSZENTRUM STIFTUNG DES OEFFENTLICHEN RECHTS, Heidelberg (DE)

(*) Notice: Subject to any disclaimer, the term of this patent is extended or adjusted under 35 U.S.C. 154(b) by 0 days.

(21) Appl. No.: 15/982,416

(22) Filed: May 17, 2018

(65) Prior Publication Data
US 2018/0256743 A1 Sep. 13, 2018

Related U.S. Application Data

(63) Continuation of application No. PCT/EP2016/078015, filed on Nov. 17, 2016.

(30) Foreign Application Priority Data

Nov. 17, 2015 (DE) .................... 10 2015 119 873.8

(51) Int. Cl.
| | |
|---|---|
| *A61P 35/00* | (2006.01) |
| *A61K 47/68* | (2017.01) |
| *C07K 14/705* | (2006.01) |
| *C12Q 1/6886* | (2018.01) |
| *A61K 31/351* | (2006.01) |
| *G01N 33/574* | (2006.01) |

(52) U.S. Cl.
CPC ........ *A61K 47/6803* (2017.08); *A61K 31/351* (2013.01); *A61P 35/00* (2018.01); *C07K 14/705* (2013.01); *C12Q 1/6886* (2013.01); *G01N 33/57407* (2013.01); *C12Q 2600/156* (2013.01); *G01N 33/574* (2013.01); *G01N 2800/56* (2013.01); *G01N 2800/60* (2013.01)

(58) Field of Classification Search
CPC .................................................. A61K 47/6803
USPC ...................................................... 424/181.1
See application file for complete search history.

(56) References Cited

U.S. PATENT DOCUMENTS

| | | | |
|---|---|---|---|
| 7,344,860 B2 * | 3/2008 | Franco ................. | C07K 14/705 435/320.1 |
| 2007/0020706 A1 | 1/2007 | Gorodeski et al. | |
| 2012/0035350 A1 | 2/2012 | Franco et al. | |

FOREIGN PATENT DOCUMENTS

WO    WO 2004/090097 A2    10/2004

OTHER PUBLICATIONS

Taglinger et al (Veterinary Immunology and Immunopathology, 2008, 122: 216-230).*
Buck et al (Biotechniques, 1999, 27(3):528-536).*
Urano, T. et al. 1997 "Cloning of P2XM, a novel human P2X receptor gene regulated by p53" *Cancer Research* 57: 3281-3287.

* cited by examiner

*Primary Examiner* — Sean E Aeder
(74) *Attorney, Agent, or Firm* — Knobbe, Martens, Olson & Bear, LLP (57) ABSTRACT

The present invention relates to a nucleic acid molecule which encodes a splice variant of the human P2RX7 receptor, and nucleic acid molecules derived therefrom, a recombinant vector containing said nucleic acid molecules, a host containing said recombinant vector, a polypeptide encoded by said nucleic acid molecules, a host cell expressing said polypeptide, a binding molecule binding to said polypeptide, a pharmaceutical composition comprising said binding molecule, a method for the production of the isolated polypeptide, and other methods and uses in connection therewith.

11 Claims, 2 Drawing Sheets

Specification includes a Sequence Listing.

```
                        SEQUENCE LISTING

<160> NUMBER OF SEQ ID NOS: 11

<210> SEQ ID NO 1
<211> LENGTH: 1586
<212> TYPE: DNA
<213> ORGANISM: Homo sapiens

<400> SEQUENCE: 1
aaaacgcagg gagggaggct gtcaccatgc cggcctgctg cagctgcagt gatgttttcc        60
agtatgagac gaacaaagtc actcggatcc agagcatgaa ttatggcacc attaagtggt       120
tcttccacgt gatcatcttt tcctacgttt gctttgctct ggtgagtgac aagctgtacc       180
agcggaaaga gcctgtcatc agttctgtgc acaccaaggt gaagggggata gcagaggtga      240 aagaggagat cgtggagaat ggagtgaaga gttggtgca cagtgtcttt gacaccgcag        300
actacacctt cccctttgcag gggaactctt tcttcgtgat gacaaacttt ctcaaaacag      360
aaggccaaga gcagcggttg tgtcccgagt atcccacccg caggacgctc tgttcctctg       420
accgaggttg taaaaaggga tggatggacc cgcagagcaa aggaattcag accggaaggt      480
gtgtagtgta tgaagggaac cagaagacct gtgaagtctc tgcctggtgc cccatcgagg       540
cagtggaaga ggccccccgg cctgctctct tgaacagtgc cgaaaacttc actgtgctca       600
tcaagaacaa tatcgacttc cccggccaca actacaccac atacgccaag tactacaagg      660
```

```
aaaacaatgt tgagaaacgg actctgataa aagtcttcgg gatccgtttt gacatcctgg    720
tttttggcac cggaggaaaa tttgacatta tccagctggt tgtgtacatc ggctcaaccc    780
tctcctactt cggtctggcc gctgtgttca tcgacttcct catcgacact tactccagta    840
actgctgtcg ctcccatatt tatccctggt gcaagtgctg tcagccctgt gtggtcaacg    900
aatactacta caggaagaag tgcgagtcca ttgtggagcc aaagccgaca ttaaagtatg    960
tgtcctttgt ggatgaatcc cacattagga tggtgaacca gcagctacta gggagaagtc   1020
tgcaagatgt caagggccaa gaagtcccaa gacctgcgat ggacttcaca gatttgtcca   1080
ggctgcccct ggccctccat gacacacccc cgattcctgg acaaccagag agatacagc    1140 tgcttagaaa ggaggcgact cctagatcca gggatagccc cgtctggtgc agtgtggaa    1200 gctgcctccc atctcaactc cctgagagcc acaggtgcct ggaggagctg tgctgccgga   1260
aaaagccggg ggcctgcatc accacctcag agctgttcag gaagctggtc ctgtccagac   1320
acgtcctgca gttcctcctg ctctaccagg agcccttgct ggcgctggat gtggattcca   1380
ccaacagccg gctgcggcac tgtgcctaca ggtgctacgc cacctggcgc ttcggctccc   1440
aggacatggc tgactttgcc atcctgccca gctgctgccg ctggaggatc cggaaagagt   1500
ttccgaagag tgaagggcag tacagtggct tcaagagtcc ttactgaagc caggcaccgt   1560
ggctcacgtc tgtaatccca cctttt                                        1586

<210> SEQ ID NO 2
<211> LENGTH: 506
<212> TYPE: PRT
<213> ORGANISM: Homo sapiens

<400> SEQUENCE: 2

Met Pro Ala Cys Cys Ser Cys Ser Asp Val Phe Gln Tyr Glu Thr Asn
1               5                   10                  15

Lys Val Thr Arg Ile Gln Ser Met Asn Tyr Gly Thr Ile Lys Trp Phe
            20                  25                  30

Phe His Val Ile Ile Phe Ser Tyr Val Cys Phe Ala Leu Val Ser Asp
        35                  40                  45

Lys Leu Tyr Gln Arg Lys Glu Pro Val Ile Ser Ser Val His Thr Lys
    50                  55                  60

Val Lys Gly Ile Ala Glu Val Lys Glu Glu Ile Val Glu Asn Gly Val
65                  70                  75                  80

Lys Lys Leu Val His Ser Val Phe Asp Thr Ala Asp Tyr Thr Phe Pro
                85                  90                  95

Leu Gln Gly Asn Ser Phe Phe Val Met Thr Asn Phe Leu Lys Thr Glu
            100                 105                 110

Gly Gln Glu Gln Arg Leu Cys Pro Glu Tyr Pro Thr Arg Arg Thr Leu
        115                 120                 125

Cys Ser Ser Asp Arg Gly Cys Lys Lys Gly Trp Met Asp Pro Gln Ser
    130                 135                 140

Lys Gly Ile Gln Thr Gly Arg Cys Val Val Tyr Glu Gly Asn Gln Lys
145                 150                 155                 160

Thr Cys Glu Val Ser Ala Trp Cys Pro Ile Glu Ala Val Glu Glu Ala
                165                 170                 175

Pro Arg Pro Ala Leu Leu Asn Ser Ala Glu Asn Phe Thr Val Leu Ile
            180                 185                 190

Lys Asn Asn Ile Asp Phe Pro Gly His Asn Tyr Thr Thr Tyr Ala Lys
        195                 200                 205
```

-continued

Tyr Tyr Lys Glu Asn Asn Val Glu Lys Arg Thr Leu Ile Lys Val Phe
        210                 215                 220
Gly Ile Arg Phe Asp Ile Leu Val Phe Gly Thr Gly Gly Lys Phe Asp
225                 230                 235                 240
Ile Ile Gln Leu Val Val Tyr Ile Gly Ser Thr Leu Ser Tyr Phe Gly
                245                 250                 255
Leu Ala Ala Val Phe Ile Asp Phe Leu Ile Asp Thr Tyr Ser Ser Asn
            260                 265                 270
Cys Cys Arg Ser His Ile Tyr Pro Trp Cys Lys Cys Gln Pro Cys
        275                 280                 285
Val Val Asn Glu Tyr Tyr Arg Lys Lys Cys Glu Ser Ile Val Glu
    290                 295                 300
Pro Lys Pro Thr Leu Lys Tyr Val Ser Phe Val Asp Glu Ser His Ile
305                 310                 315                 320
Arg Met Val Asn Gln Gln Leu Leu Gly Arg Ser Leu Gln Asp Val Lys
                325                 330                 335
Gly Gln Glu Val Pro Arg Pro Ala Met Asp Phe Thr Asp Leu Ser Arg
            340                 345                 350
Leu Pro Leu Ala Leu His Asp Thr Pro Pro Ile Pro Gly Gln Pro Glu
        355                 360                 365
Glu Ile Gln Leu Leu Arg Lys Glu Ala Thr Pro Arg Ser Arg Asp Ser
    370                 375                 380
Pro Val Trp Cys Gln Cys Gly Ser Cys Leu Pro Ser Gln Leu Pro Glu
385                 390                 395                 400
Ser His Arg Cys Leu Glu Glu Leu Cys Cys Arg Lys Lys Pro Gly Ala
                405                 410                 415
Cys Ile Thr Thr Ser Glu Leu Phe Arg Lys Leu Val Leu Ser Arg His
            420                 425                 430
Val Leu Gln Phe Leu Leu Leu Tyr Gln Glu Pro Leu Leu Ala Leu Asp
        435                 440                 445
Val Asp Ser Thr Asn Ser Arg Leu Arg His Cys Ala Tyr Arg Cys Tyr
    450                 455                 460
Ala Thr Trp Arg Phe Gly Ser Gln Asp Met Ala Asp Phe Ala Ile Leu
465                 470                 475                 480
Pro Ser Cys Cys Arg Trp Arg Ile Arg Lys Glu Phe Pro Lys Ser Glu
                485                 490                 495
Gly Gln Tyr Ser Gly Phe Lys Ser Pro Tyr
            500                 505

<210> SEQ ID NO 3
<211> LENGTH: 1853
<212> TYPE: DNA
<213> ORGANISM: Homo sapiens

<400> SEQUENCE: 3
aaaacgcagg gagggaggct gtcaccatgc cggcctgctg cagctgcagt gatgttttcc        60
agtatgagac gaacaaagtc actcggatcc agagcatgaa ttatggcacc attaagtggt       120
tcttccacgt gatcatcttt tcctacgttt gctttgctct ggtgagtgac aagctgtacc       180
agcggaaaga gcctgtcatc agttctgtgc acaccaaggt gaaggggata gcagaggtga       240
aagaggagat cgtggagaat ggagtgaaga agttggtgca cagtgtcttt gacaccgcag       300
actacacctt cccctttgcag gggaactctt tcttcgtgat gacaaacttt ctcaaaacag       360
aaggccaaga gcagcggttg tgtccgagt atcccacccg caggacgctc tgttcctctg       420

```
accgaggttg taaaaaggga tggatggacc cgcagagcaa aggaattcag accggaaggt    480
gtgtagtgta tgaagggaac cagaagacct gtgaagtctc tgcctggtgc cccatcgagg    540
cagtggaaga ggccccccgg cctgctctct tgaacagtgc cgaaaacttc actgtgctca    600
tcaagaacaa tatcgacttc cccggccaca actacaccac gagaaacatc ctgccaggtt    660
taaacatcac ttgtaccttc acaagactc agaatccaca gtgtcccatt ttccgactag     720
gagacatctt ccgagaaaca ggcgataatt tttcagatgt ggcaattcag gcggaataa     780 tgggcattga gatctactgg gactgcaacc tagaccgttg gttccatcac tgccatccca    840
aatacagttt ccgtcgcctt gacgacaaga ccaccaacgt gtccttgtac cctggctaca    900
acttcagata cgccaagtac tacaaggaaa acaatgttga aaacggact ctgataaaag     960 tcttcgggat ccgttttgac atcctggttt ttggcaccgg aggaaaattt gacattatcc   1020
agctggttgt gtacatcggc tcaaccctct cctacttcgg tctggccgct gtgttcatcg   1080
acttcctcat cgacacttac tccagtaact gctgtcgctc ccatatttat ccctggtgca   1140
agtgctgtca gccctgtgtg gtcaacgaat actactacag gaagaagtgc gagtccattg   1200
tggagccaaa gccgacatta aagtatgtgt cctttgtgga tgaatcccac attaggatgg   1260
tgaaccagca gctactaggg agaagtctgc aagatgtcaa gggccaagaa gtcccaagac   1320
ctgcgatgga cttcacagat ttgtccaggc tgccccctggc cctccatgac acaccccga   1380 ttcctggaca accagaggag atacagctgc ttagaaagga ggcgactcct agatccaggg   1440
atagccccgt ctggtgccag tgtggaagct gcctcccatc tcaactccct gagagccaca   1500
ggtgcctgga ggagctgtgc tgccggaaaa agccgggggc ctgcatcacc acctcagagc   1560
tgttcaggaa gctggtcctg tccagacacg tcctgcagtt cctcctgctc taccaggagc   1620
ccttgctggc gctggatgtg gattccacca acagccggct gcggcactgt gcctacaggt   1680
gctacgccac ctggcgcttc ggctcccagg acatggctga cttttgccatc ctgcccagct   1740 gctgccgctg gaggatccgg aaagagtttc gaagagtga agggcagtac agtggcttca   1800
agagtcctta ctgaagccag gcaccgtggc tcacgtctgt aatcccacct ttt          1853
```

<210> SEQ ID NO 4
<211> LENGTH: 267
<212> TYPE: DNA
<213> ORGANISM: Homo Sapiens

<400> SEQUENCE: 4

```
gagaaacatc ctgccaggtt taaacatcac ttgtaccttc acaagactc agaatccaca      60 gtgtcccatt ttccgactag gagacatctt ccgagaaaca ggcgataatt tttcagatgt    120
ggcaattcag gcggaataa tgggcattga gatctactgg gactgcaacc tagaccgttg    180
gttccatcac tgccatccca aatacagttt ccgtcgcctt gacgacaaga ccaccaacgt    240
gtccttgtac cctggctaca acttcag                                        267
```

<210> SEQ ID NO 5
<211> LENGTH: 595
<212> TYPE: PRT
<213> ORGANISM: Homo sapiens

<400> SEQUENCE: 5

```
Met Pro Ala Cys Cys Ser Cys Ser Asp Val Phe Gln Tyr Glu Thr Asn
1               5                   10                  15

Lys Val Thr Arg Ile Gln Ser Met Asn Tyr Gly Thr Ile Lys Trp Phe
```

```
            20                  25                  30
Phe His Val Ile Ile Phe Ser Tyr Val Cys Phe Ala Leu Val Ser Asp
                35                  40                  45

Lys Leu Tyr Gln Arg Lys Glu Pro Val Ile Ser Ser Val His Thr Lys
 50                  55                  60

Val Lys Gly Ile Ala Glu Val Lys Glu Glu Ile Val Glu Asn Gly Val
 65                  70                  75                  80

Lys Lys Leu Val His Ser Val Phe Asp Thr Ala Asp Tyr Thr Phe Pro
                85                  90                  95

Leu Gln Gly Asn Ser Phe Phe Val Met Thr Asn Phe Leu Lys Thr Glu
                100                 105                 110

Gly Gln Glu Gln Arg Leu Cys Pro Glu Tyr Pro Thr Arg Arg Thr Leu
                115                 120                 125

Cys Ser Ser Asp Arg Gly Cys Lys Lys Gly Trp Met Asp Pro Gln Ser
                130                 135                 140

Lys Gly Ile Gln Thr Gly Arg Cys Val Val Tyr Glu Gly Asn Gln Lys
145                 150                 155                 160

Thr Cys Glu Val Ser Ala Trp Cys Pro Ile Glu Ala Val Glu Glu Ala
                165                 170                 175

Pro Arg Pro Ala Leu Leu Asn Ser Ala Glu Asn Phe Thr Val Leu Ile
                180                 185                 190

Lys Asn Asn Ile Asp Phe Pro Gly His Asn Tyr Thr Thr Arg Asn Ile
                195                 200                 205

Leu Pro Gly Leu Asn Ile Thr Cys Thr Phe His Lys Thr Gln Asn Pro
                210                 215                 220

Gln Cys Pro Ile Phe Arg Leu Gly Asp Ile Phe Arg Glu Thr Gly Asp
225                 230                 235                 240

Asn Phe Ser Asp Val Ala Ile Gln Gly Gly Ile Met Gly Ile Glu Ile
                245                 250                 255

Tyr Trp Asp Cys Asn Leu Asp Arg Trp Phe His His Cys Arg Pro Lys
                260                 265                 270

Tyr Ser Phe Arg Arg Leu Asp Asp Lys Thr Thr Asn Val Ser Leu Tyr
                275                 280                 285

Pro Gly Tyr Asn Phe Arg Tyr Ala Lys Tyr Tyr Lys Glu Asn Asn Val
                290                 295                 300

Glu Lys Arg Thr Leu Ile Lys Val Phe Gly Ile Arg Phe Asp Ile Leu
305                 310                 315                 320

Val Phe Gly Thr Gly Gly Lys Phe Asp Ile Ile Gln Leu Val Val Tyr
                325                 330                 335

Ile Gly Ser Thr Leu Ser Tyr Phe Gly Leu Ala Ala Val Phe Ile Asp
                340                 345                 350

Phe Leu Ile Asp Thr Tyr Ser Ser Asn Cys Cys Arg Ser His Ile Tyr
                355                 360                 365

Pro Trp Cys Lys Cys Cys Gln Pro Cys Val Val Asn Glu Tyr Tyr Tyr
                370                 375                 380

Arg Lys Lys Cys Glu Ser Ile Val Glu Pro Lys Pro Thr Leu Lys Tyr
385                 390                 395                 400

Val Ser Phe Val Asp Glu Ser His Ile Arg Met Val Asn Gln Gln Leu
                405                 410                 415

Leu Gly Arg Ser Leu Gln Asp Val Lys Gly Gln Glu Val Pro Arg Pro
                420                 425                 430

Ala Met Asp Phe Thr Asp Leu Ser Arg Leu Pro Leu Ala Leu His Asp
                435                 440                 445
```

```
Thr Pro Pro Ile Pro Gly Gln Pro Glu Glu Ile Gln Leu Leu Arg Lys
    450                 455                 460
Glu Ala Thr Pro Arg Ser Arg Asp Ser Pro Val Trp Cys Gln Cys Gly
465                 470                 475                 480
Ser Cys Leu Pro Ser Gln Leu Pro Glu Ser His Arg Cys Leu Glu Glu
                485                 490                 495
Leu Cys Arg Lys Lys Pro Gly Ala Cys Ile Thr Thr Ser Glu Leu
            500                 505                 510
Phe Arg Lys Leu Val Leu Ser Arg His Val Leu Gln Phe Leu Leu Leu
            515                 520                 525
Tyr Gln Glu Pro Leu Leu Ala Leu Asp Val Asp Ser Thr Asn Ser Arg
    530                 535                 540
Leu Arg His Cys Ala Tyr Arg Cys Tyr Ala Thr Trp Arg Phe Gly Ser
545                 550                 555                 560
Gln Asp Met Ala Asp Phe Ala Ile Leu Pro Ser Cys Cys Arg Trp Arg
                565                 570                 575
Ile Arg Lys Glu Phe Pro Lys Ser Glu Gly Gln Tyr Ser Gly Phe Lys
            580                 585                 590
Ser Pro Tyr
    595

<210> SEQ ID NO 6
<211> LENGTH: 20
<212> TYPE: DNA
<213> ORGANISM: Artificial Sequence
<220> FEATURE:
<223> OTHER INFORMATION: primer

<400> SEQUENCE: 6 ggttttggc accggaggaa                                              20

<210> SEQ ID NO 7
<211> LENGTH: 20
<212> TYPE: DNA
<213> ORGANISM: Artificial Sequence
<220> FEATURE:
<223> OTHER INFORMATION: primer

<400> SEQUENCE: 7
ccactgtact gcccttcact                                             20

<210> SEQ ID NO 8
<211> LENGTH: 20
<212> TYPE: DNA
<213> ORGANISM: Artificial Sequence
<220> FEATURE:
<223> OTHER INFORMATION: primer

<400> SEQUENCE: 8
ctctgctcct cctgttcgac                                             20

<210> SEQ ID NO 9
<211> LENGTH: 20
<212> TYPE: DNA
<213> ORGANISM: Artificial Sequence
<220> FEATURE:
<223> OTHER INFORMATION: primer

<400> SEQUENCE: 9
ttaaaagcag ccctggtgac                                             20
```

```
<210> SEQ ID NO 10
<211> LENGTH: 18
<212> TYPE: DNA
<213> ORGANISM: Artificial Sequence
<220> FEATURE:
<223> OTHER INFORMATION: primer

<400> SEQUENCE: 10
gcccgaaacg ccgaatat                                                 18

<210> SEQ ID NO 11
<211> LENGTH: 18
<212> TYPE: DNA
<213> ORGANISM: Artificial Sequence
<220> FEATURE:
<223> OTHER INFORMATION: primer

<400> SEQUENCE: 11
ccgtggttcg tggctctc                                                 18
```

TUMOR MARKER FOR THE RHABDOMYOSARCOMA

CROSS-REFERENCES TO RELATED APPLICATIONS

This application is a continuation of copending international patent application PCT/EP2016/078015 filed on 17 Nov. 2016 and designating the U.S., which has been published in English, and claims priority from German patent application DE 10 2015 119 873.8 filed on 17 Nov. 2015. The entire contents of these prior applications are incorporated herein by reference.

REFERENCE TO A SEQUENCE LISTING

A Sequence Listing submitted as an ASCII text file via EFS-Web is hereby incorporated by reference in accordance with 35 U.S.C. § 1.52(e). The name of the ASCII text file for the Sequence Listing is 28299585_1.txt, the date of creation of the ASCII text file is May 17, 2018, and the size of the ASCII text file is approximately 15.8 KB. The information in the electronic format of the Sequence Listing is incorporated herein by reference in its entirety.

FIELD OF THE INVENTION

The present invention relates to a nucleic acid molecule which encodes a splice variant of the human P2RX7 receptor, and nucleic acid molecules derived therefrom, a recombinant vector containing said nucleic acid molecules, a host containing said recombinant vector, a polypeptide encoded by said nucleic acid molecules, a host cell expressing said polypeptide, a binding molecule binding to said polypeptide, a pharmaceutical composition comprising said binding molecule, a method for the production of the isolated polypeptide, and other methods and uses in connection therewith.

The invention relates to the field of molecular biology and molecular medicine, in particular the diagnosis and treatment of tumors, including the rhabdomyosarcoma (RMS).

BACKGROUND OF THE INVENTION

The rhabdomyosarcoma (RMS) is the third most extracranially located malign tumor and the most frequent soft tissue sarcoma in childhood. The RMS belongs to the malignant soft tissue sarcoma. It consists of not matured mesenchyme cells which are intended for a differentiation into skeleton muscle cells but show a disrupted myogenesis and, as a result, degenerate into malignant cells. Very often the metastasis occurs into the lung, the bone marrow, the bones and the regional lymph nodes.

Histologically it is differentiated between the embryonic and alveolar forms of RMS which significantly differ from each other in their tumor biology. The embryonic RMS is characterized by a "more benign" progress with a rarer tendency to metastasis, whereas the alveolar RMS very often metastasizes.

The current therapy of RMS consists of a multimodal treatment with a systemic chemotherapy, radiation therapy, and tumor resection. The intensity and radicalism of the therapy is determined on the basis of a corresponding risk stratification based on histology, post surgical tumor stadium according to the IRS classification ("Intergroup Rhabdomyosarcoma Study"), status of the lymph nodes, the size of the tumor, and the age of the patients.

Despite the interdisciplinary therapy concepts the prognosis, in particular for the alveolar subtype and in advanced tumor stages, is poor. The prognosis of the affected children in the stadium IV which is characterized by remote metastases is poor, with a 5 year survival rate of 27% and with a tumor recurrence with a 5 year survival rate of 21%. The current options for therapy are unlikely to result in a further improvement of the prognosis. For this reason, the search for new, innovative therapeutic approaches is of the outmost importance.

Against this background it is an object underlying the invention to identify or provide new target structures or biomarkers, respectively, which provide the basis for a selective diagnosis and therapy.

SUMMARY OF THE INVENTION

This object is met by a nucleic acid molecule which comprises a polynucleotide with a nucleotide sequence which is selected from the group consisting of:
  (a) SEQ ID No. 1;
  (b) nucleotide sequence which, due to the degeneration of the genetic code, encodes the same amino acid sequence as SEQ ID No. 1;
  (c) nucleotide sequence which is complementary to SEQ ID No. 1;
  (d) nucleotide sequence which encodes the exons 1-6 and 9-13, however not the exons 7 and 8, of the human P2RX7 gene;
  (e) nucleotide sequence comprising the codons p1-205 and p.295-595 encoding the human P2RX7 gene;
  (f) nucleotide sequence comprising all of the codons encoding the human P2RX7 gene minus the codons p.206-294;
  (g) nucleotide sequence encoding the amino acid sequence of SEQ ID No. 2;
  (h) nucleotide sequence which, under stringent conditions, hybridizes to any of the nucleotide sequences (a) to (g).

The claimed nucleic acid molecule encodes a cell structure or parts thereof, which, as such, were identified by the inventors, and via which cells of the rhabdomyosarcoma can be addressed in a highly specific and selective manner. As examinations of the inventors were able to demonstrate the cell structure is a new splice variant of the so-called P2X7 receptor or derivatives thereof.

Normally P2X receptors can primarily be found in neurons, neuroglia, the endothelium and epithelium, muscles, bones, and hematopoetic tissues. From a functional standpoint they are ion channels which open as a function of ATP. They consist of several subunits of membrane proteins which, in turn, each consists of two transmembrane domains with an adjacent intra- and extracellular domain. In total, seven different subunits with amino acid sequences which are identical up to 50% are described. The major part of the receptors of this family are homomers of three identical subunits each.

In parts the individual receptors belonging to the P2X family differ significantly. While the ATP-depending activation and the permeability for small monovalent cations is shared by all receptors of P2X family only the P2X7 receptor is capable to control the induction of apoptotic processes via a destabilization of the cell membrane ("large pore formation") and intracellular signal cascades which are so far in parts well examined. Furthermore, the P2X7 receptor is involved in the control of cell proliferation and the adaptation of the cell organism to inflammation and ischemia. Even though the signal transduction pathways are not completely understood, it seems that both the duration of the receptor stimulation as well as the ATP concentration in the respective tissue seem to play a key role. The presence of P2X7 receptors in the wild-type variant is predominantly limited to mesenchymal, epithelial, hematopoetic and neuronal cell lines.

The gene of the human P2X7 receptor includes thirteen exons and is located on the chromosome 12q24. It encodes 595 amino acids. The mRNA of the P2X7 receptor of *Homo sapiens* in the wild type is deposited under the GenBank Lokus Y09561.1. It consists of 1853 base pairs.

Several splice variants of this sequence are known so far, see Slyter and Stokes (2011), Significance of P2X7 Receptor Variants to Human Health and Disease. Recent Patents on DNA and Gene Sequences, Vol. 5, pages 41 to 54. The splice variant of the P2X7 receptor according to the invention is, however, not described in the state of the art.

According to the findings of the inventors the new splice variant of the P2X7 receptor is the first tumor marker specific for RMS.

Other than the splice variants of the P2X7 receptor knows so far the RNA transcript of the variant according to the invention does not comprise an early stop codon. For this reason it is also not subject of the nonsense-mediated decay (NMD), a mechanism with the consequence that no or only few amounts of the shortened proteins are produced.

The variant of the P2X7 receptor according to the invention is expressed on the cell surface of RMS cells. For this reason, it is a preferential target structure for a targeted diagnostics or therapy, for example on the basis of specific antibodies.

SEQ ID No. 1 from the enclosed sequence listing is the nucleotide sequence of the new splice variant. The amino acid sequence of the splice variant of the human P2X7 receptor according to the invention is shown in the SEQ ID No. 2 of the sequence listing.

The inventors were able to find that the new splice variant of the P2X7 receptor encodes the exons 1 to 6 and 9 to 13, however not the exons 7 and 8 of the human P2RX7 gene in the wild type. As a consequence, the amino acids at the positions 1 to 205 and 295 to 595 of the human P2RX7 gene are encoded, however not the amino acids at the positions 206 to 294.

According to the invention "stringent conditions" are to be understood as referring to such conditions where only such nucleotide sequences hybridize with each other which comprise perfect or almost perfect (95%) complementarity. Stringent conditions are known to the skilled person and can for example be found in "Current Protocols in Molecular Biology", John Wiley and Sons, N.Y. (1989), 6.3.1 to 6.3.6.

The object underlying the invention is herewith completely met.

Another subject matter of the invention is a recombinant vector comprising the nucleic acid molecule according to the invention.

The recombinant vector can be a replication vector, transfer vector, expression vector etc. The vector according to the invention creates the constructive preconditions for a replication and/or expression of the nucleic acid molecule according to the invention.

An even further subject matter of the present invention is a host cell comprising the recombinant vector according to the invention.

The host cell can be any procaryotic or eucaryotic cell capable for the receipt and, if applicable, the replication and expression of the recombinant vector. It allows the replication and/or expression of the nucleic acid molecule according to the invention. Examples of appropriate procaryotic cells or systems are *Escherichia coli* and *Bacillus subtilis*. Examples of appropriate eucaryotic cells or systems are yeasts, mammalian cells such as CHO and myeloma cells, and insect cells such as Sf-9, Sf-21 together with a Baculovirus expression system.

Another subject matter of the present invention is a polypeptide comprising an amino acid sequence which is selected from the group consisting of:
  (a) SEQ ID No. 2;
  (b) amino acid sequence encoded by the nucleic acid molecule according to the invention.

A variant of the polypeptide according to the invention comprises one or several sequential amino acid deletions at the C terminus and/or the N terminus.

Also such a polypeptide is suitable to generate a binding molecule, for example an antibody, which can bind to the new splice variant of the P2X7 receptor and, for this reason, is part of the invention. According to the invention, "several" sequential amino acid deletions comprise maximum 10, preferably maximum 9, 8, 7, 6, 5, 4, 3, 2 sequential amino acid deletions, at the C terminus and/or at the N terminus.

Another subject matter of the present invention relates to a host cell which expresses the polypeptide according to the invention.

Here the recitals mentioned for the host cell which contains the recombinant vector according to the invention, apply correspondingly.

Another subject matter of the present invention relates to a binding molecule, preferably an antibody, further preferably a monoclonal antibody, which specifically binds to the polypeptide according to the invention.

This subject matter of the invention represents the preconditions for a targeted diagnostics or therapy of the RMS and, for this reason, is one of the central subject matter of the present invention. The production of such a binding molecule or antibody, respectively, is realized by methods generally known in the state of the art. Further binding molecules encompassed by the invention are aptamers or lower molecular components ("small molecules") with high affinity for the new splice variant of the human P2X7 receptor. According to the invention, "specific" means that the binding molecule can selectively bind to the polypeptide according to the invention, thus also to the new splice variant of the human P2X7 receptor. "Specific" also means in this context that the binding molecule according to the invention cannot bind to the wild type of the human P2X7 receptor.

In an embodiment of the invention the binding molecule according to the invention is coupled with a cytotoxic agent, preferably doxorubicin.

With this configuration of the binding molecule according to the invention RMS cells can be killed in a targeted manner. A "cytotoxic agent" refers to substances which have a detrimental impact on the physiological cellular processes or kill the cell, respectively. They also include the group of cytostatics among which doxorubicin is of particular preference.

Another subject matter of the present invention relates to a pharmaceutical composition which comprises the binding molecule according to the invention and a pharmaceutically acceptable carrier.

Pharmaceutically acceptable carrier are well-known in the state of the art. In an exemplary manner it is referred to Kibbe A. (2003), Handbook of Pharmaceutical Excipients, 4th edition, American Pharmaceutical Association and Pharmaceutical Press. The pharmaceutical composition according to the invention can also contain additives. They encompass any compound or composition which are advantageous for the effectiveness of the binding molecule according to the invention, which include salts, binders, solvents, dispersing agents, adjuvants and further compounds usually used in the context of the formulation of binding molecules.

Another subject matter of the present invention relates to a method for the production of an isolated polypeptide, comprising the following steps:
  (a) Cultivating the host cell according to the invention under such conditions where the polypeptide is expressed;
  (b) isolating the polypeptide.

Conditions allowing the expression of the polypeptide according to the invention are well-known to the skilled person.

A still further subject matter of the present invention relates to the use of the nucleic acid molecule according to the invention and/or the polypeptide according to the invention and/or the binding molecule according to the invention, for the detection and/or the diagnosis of a tumor, preferably a rhabdomyosarcoma, further preferably an embryonic rhabdomyosarcoma.

A still further subject matter of the present invention relates to the use of the binding molecule according to the invention or the pharmaceutical composition according to the invention, for the treatment and/or prophylaxis of a tumor, preferably a rhabdomyosarcoma, further preferably an embryonic rhabdomyosarcoma.

Another subject matter of the present invention relates to a method for the detection and/or for the diagnosis of a tumor in a living being, preferably a rhabdomyosarcoma, further preferably an embryonic rhabdomyosarcoma (RMS), comprising the following steps:
  (a) Providing a biological sample originating from the living being,
  (b) Examining the biological sample for the presence or the absence of the nucleic acid molecule according to the invention and/or the polypeptide according to the invention,
  (c) Positive detection and/or making a positive diagnosis in case of the presence, or negative detection and/or making a negative diagnosis in case of the absence.

In an embodiment of the invention the biological sample is a tissue sample from an area of the living being where the RMS is suspected to be. The examination for the presence or the absence of the nucleic acid molecule according to the invention and/or the polypeptide according to the invention is realized by methods known to the skilled person, including antibody-based detection methods, such as ELISA, immunoblot method, etc., nucleic-acid based detection methods, such as the Northern blot method, etc.

A still further subject matter of the present invention relates to a method for the treatment and/or prophylaxis of a tumor in a living being, preferably a rhabdomyosarcoma, further preferably an embryonic rhabdomyosarcoma, comprising the administration of the binding molecule according to the invention or the pharmaceutical composition according to the invention into the living being.

According to invention the living being can be an animal or human living being.

It shall be understood that the features mentioned above and those to be mentioned in the following cannot only be used in the combination indicated in each case but also in other combinations or in isolated position without departing from the scope of the present invention.

The invention is now explained in more details by means of embodiments which result in further characteristics, features and advantages. The embodiments are purely illustrative and do not restrict the scope of the invention. Features which are described in connection with a specific embodiment are isolated features of the invention in its general form and are not only features in the specific technical context.

Reference is made to the enclosed figures.

DESCRIPTION OF PREFERRED EMBODIMENTS

1. Material and Methods 1.1 Cell Lines and Cultivation Conditions

The human embryonic RMS cell line RD (ATCC, Manassas, Va., USA), the alveolar RMS cell line Rh30 (DSMZ, Braunschweig, Germany) and the skeleton muscle cells (SKMCs; Promokine, Heidelberg, Germany) are cultivated according to the information of the manufacturer in DMEM high glucose medium, supplemented with 10% fetal bovine serium, 1% penicillin/streptomycin and 1% L-glutamine (all from Biochrom, Berlin, Germany), in a humid atmosphere at 37° C. and 5% $CO_2$. All cells were negative for mycoplasms. The cell identity was verified by SLR analysis of the DNA profile by using a PowerPlex 16 (Promega, Mannheim, Germany).

1.2 PCR of the P2XR7 Expression in Tissue Samples of Patients

To determine the presence of mRNA of the P2X7 receptor from cryo-preserved tissue samples RNA was extracted by using the NucleoSpin® RNA/DNA buffer set (Machery & Nagel, Düren, Germany) according to the information of the manufacturer. After a DNAse-digestion 2 µg of total RNA was reversely transcribed into cDNA by using the high capacity reverse transcription kit (Life Technologies, Carlsbad, Calif., USA). A PCR was performed by using the geneeAmp® PCR system 9700 (Applied Biosystems, Darmstadt, Germany), by using 10 pmol/µl forward and backward primers and 2× GoTaq® Master Mix (Promega Corporation, Madison, Wis., USA) according to the protocol of the manufacturer. The cyclation conditions were as follows: initial denaturation at 95° C. for 2 minutes, followed by 35 cycles at 95° C. for 45 seconds, 60° C. for 45 seconds and 72° C. for 90 seconds. For the amplification of the tissue samples of the patients the following primers were used (5'→3'-orientation):

```
P2XR7,
fw:
                              [SEQ ID No. (6)]
GGT TTT TGG CAC CGG AGG AA
and rev:
                              [SEQ ID No. (7)]
CCA CTG TAC TGC CCT TCA CT
```

The transcript level of GAPDH as a housekeeping gene was determined for each sample by using the following primers (5'→3'-orientation):

```
GAPDH,
fw:
                                      [SEQ ID No. (8)]
CTC TGC TCC TCC TGT TCG AG
and rev:
                                      [SEQ ID No. (9)]
TTA AAA GCA GCC CTG GTG AC
```

1.3 Real Time PCR of the P2XR7 Expression in RMS Cell Lines

To determine the mRNA abundance of the P2RX7 total cellular RNA was extracted from the human embryonic RMS cell line RD (ATCC, Manassas, Va., USA), the alveolar RMS cell line Rh30 and human skeleton muscle cells (SKMCs; Promokine, Heidelberg, Germany) using the RNeasy-Minikits (Qiagen, Hilden, Germany) according to the manufacturer's instructions. After a DNA digestion approximately 2.5 µg of total RNA was revers transcribed to cDNA using High Capacity cDNA Reverse Transcription Kits (Life technologies, Carlsbad, Calif., USA). A quantitative real time PCR was applied on the CFX96 Real-Time System (Biorad) using 500 nm forward and reverse primer and 2× GoTaq® qPCR Master Mix (Promega Corporation, Madison, Wis., USA) according to the manufacturer's protocol. The cycling conditions were as follows: initial denaturation at 95° C. for 5 minutes, followed by 40 cycles of 95° C. for 15 seconds, 57° C. for 1 minute and 72° C. for 30 seconds. For the amplification of human RD and Rh30 cells the following primers were used (5'-3'-orientation):

```
P2XR7,
fw:
                                      [SEQ ID No. (6)]
GGT TTT TGG CAC CGG AGG AA
and rev:
                                      [SEQ ID No. (7)]
CCA CTG TAC TGC CCT TCA CT.
```

The transcript level of the TATA box binding protein (TBP) as a housekeeping gene was determined for each sample by using the following primers (5'→3'-orientation):

```
TBP,
fw
                                     [SEQ ID No. (10)]
GCC CGA AAC GCC GAA TAT
and rev:
                                     [SEQ ID No. (11)]
CCG TGG TTC GTG GCT CTC
```

The specificity of the PCR product was confirmed by the analysis of a melting curve. All experiments were done in duplicate. The relative quantification of the gene expression was achieved by using the Δct method.

1.4 Purification of the PCR Product from the Agarose Gel

After the amplification 20 µl of each RT PCR product of the RMS cell lines and the PCR product of the patient tumor samples were electrophoresed through a 2% agarose gel (Biozym, Oldendorf, Germany) in 1% TAE (40 mM Tris Base, 20 mM acetic acid, 1 mM EDTA) electrophoresis buffer for 1 hour at 100 V. The short and the long bands of the gel PCR products were purified by using the Min Elute Gel Extraktion Kits (Qiagen, Hilden, Germany) and a portion of the PCR products from each sample was sent to DNA sequencing for both sense and anti-sense orientations to Biosequence Source.

1.5 Gene Expression Analysis

The gene expressions data were subject of a micro array analysis. All patients were treated within the trials of the Cooperative Soft Tissue Sarcoma Study (CWS) Group of the Society of Pediatric Oncology and Hematology (GPOH). The mean age of the patients was 6.4 years (range 1 to 15 years, 95% Cl of mean 4.2 to 8.8). The histological analysis revealed 5 RMA and 6 RME. All cases received a central pathological review and the patients were treated according to uniform protocols. Only samples with a tumor content of at least 80% were included into the analysis. The metastases were present at the time of surgery in all patients suffering from RMA and in non-RME-patients. The analysis of the tissue samples was improved by the local ethical comittee. (CWS 2002-P: 418/2004V). As controls, data of skeleton muscle biopsies from 8 patients acquired on the same array platform were used. The expression of P2RX7 (probe set 207091_at on the Affymetrix HG-U133 Plus 2.0 microarray) was compared with the housekeeping gene GAPDH (212581_x_at and 213453_x_at) for each sample as fraction of the signal log ratio. The comparison of the relative expression in RMA, RME and control muscle tissue was performed by the student's t-test.

2. Results 2.1 PCR and Gel Electrophoresis

Figure 1:
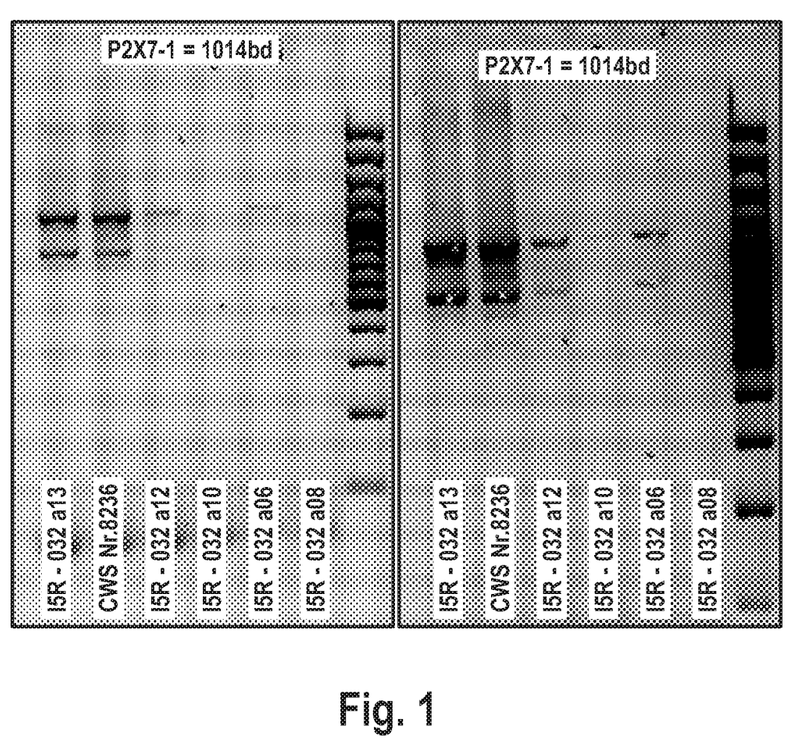
FIG. 1 Representation of the gel electrophoresis of the PCR product after amplification with corresponding P2X7 primers with an apparent double band. Already in the initial sequencing of the PCR product a loss of 267 base pairs was determined. After "picking" the DNA, renewed amplification and sequencing the result could be confirmed.

In the run-up to the evaluation of a new antibody against inactivated P2X7 receptors (nf-P2X7 receptors) already known in the prior art, the expression of P2X7 receptors on cryo-stored RMS cells of the department internal tumor bank should be evaluated. On this occasion after the amplification of the DNA via RT-PCR in the vast majority of the samples in the context of the gel electrophoresis a double band of the PCR product was detected. This was reproducible in several experiments. The result is shown in FIG. 1.

After the sequencing of the corresponding cDNA it was shown that the short band corresponds to a new P2X7 sequence with a deletion of 267 base pairs which is expressed simultaneously with the wild type sequence in the RMS tumor. In a repeated sequencing with another primer the result was again reproducible. So far the correspondingly shortened sequence could also not be detected in any other examined tumor entity (of other soft tissue sarcomas).

2.2 Sequencing

The sequencing of the cDNA encoding for the new splice variant of the P2X7 receptor resulted in the nucleotide sequence which is shown in the attached sequence listing under SEQ ID No. 1. The corresponding amino acid sequence is shown under SEQ ID No. 2. The nucleotide sequence of a cDNA encoding for the wild type of the human P2X7 receptor is shown under SEQ ID No. 3 in the enclosed sequence listing.

There is a gap of 267 bases in length in the alignment of the cDNA against the mRNA sequence of the P2RX7 wild type or main transcript: ENST00000328963 122 to 757 (+) and ENST00000328963 1025 to 1964 (+). The nucleotide sequence of the missing 267 bases is shown under SEQ ID No. 4. The alignments of both parts are (with the exception of the gap) perfect, i.e. without another alteration with respect to the mRNA consensus reference sequence GenBank locus Y09561.1 or the newest geneom/transcriptom version GRCh38/Ensembl67.

2.2.1 Effects of the Observed cDNA Alignment on the Transcript

In the cDNA alignment the exons 7 and 8 (out of 13 exons in total) are completely missing. The Exon 6 is directly spiced to the Exon 9. The missing of exons 7 and 8 result in a change of the base after the splice position (first base Exon 7=G; first base Exon 9=A).

2.2.2 Effects of the Observed cDNA Alignments on the Amino Acid Sequence of the Protein The splice variant does not result in a frame shift (shift of the codon reading frame): Exon 6 end: codon reading frame raster 2; Exon 9 start: codon reading frame raster 2.

The variant does not result in a change of the amino acid at the splice position, because the changed base does not result in a change of the amino acid:

mRNA wild type codon: c.756, c.757, c.758=ACG=Thr
mRNA cDNA codon: c.756, c. 757, c.1025=ACA=Thr The amino acid sequence (SEQ ID No. 2) is shortened by the corresponding amino acids (89) encoded by exons 7+8, but otherwise is complete. The amino acid sequence of the wild type of the P2X7 receptor protein is shown in the SEQ ID No. 5.

2.3 Evaluation

The alignment of the observed cDNA results in a deletion of the exons 7 and 8 in the only protein encoding RNA transcript of the P2X7 receptor gene which is so far known. Thereby the reading frame of the remaining exons (9 to 13) is preserved so that the protein translation in the following will take place until the wild type stop codon is reached. Consequently, an altered P2X7 receptor protein translated from the observed cDNA would be shortened by 89 of the 595 amino acids in total encoded in the codons p.206-p.294.

Figure 2:
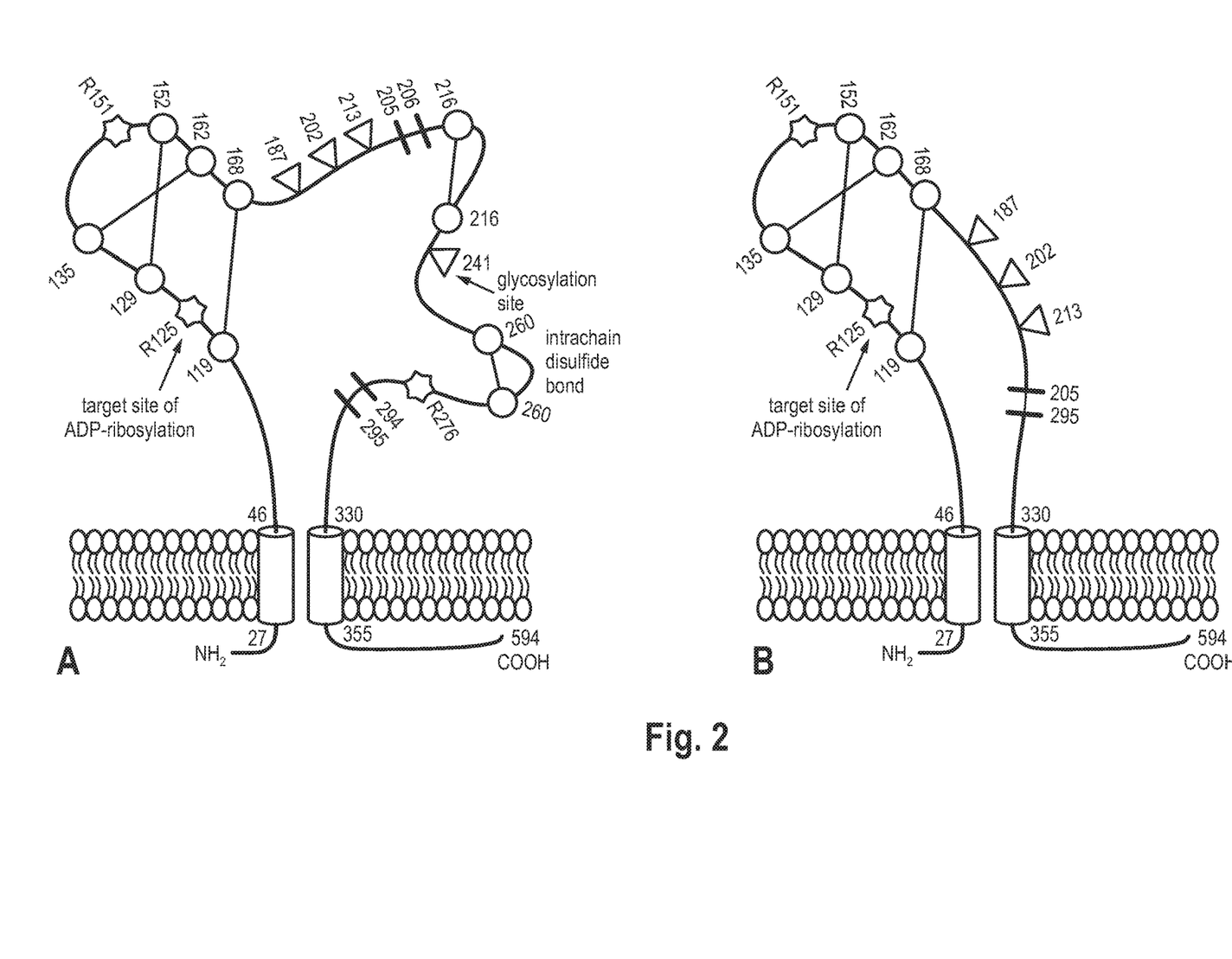
FIG. 2 shows the human P2X2 receptor in the wild type (A) and in correspondence to the new splice variant (B), each embedded into the membrane, in an illustrative graph.

Because the observed cDNA is shortened correspondingly but no early stop codon is generated it can be assumed that the correspondingly shortened protein is also translated and, as a consequence, produced in the tumor. In FIG. 2 it is shown how the variant (B; right) in comparison to the wild type (A; left) could be embedded into the cell membrane of RMS cells.

So far no RNA transcript of P2RX7 is known which corresponds to the observed cDNA.

Among the known RNA transcripts there is one with the identical deletion of the codons p.206-p.294. The affected transcript, however, shows additional further splice variants which generate an early stop codon at the position p.365 and consequently trigger the "Non Sense Mediated mRNA Decay" (NMD).

3. Conclusion

The existence of a specific surface marker on tumors is of significance in many respects. Besides a use in the context of establishing a new tumor marker and a possible tool for the risk stratification of pediatric tumor patients from a technical point of view the synthesis of a specific capture molecule, such as an antibody, against the splice variant is possible. The use of such an antibody promises new options in the diagnostics and therapy of childhood RMS and possibly further tumors in the long run.

SEQUENCES

SEQ ID No. 1 nucleotide sequence cDNA of the new splice variant of the P2X7 receptor
SEQ ID No. 2 amino acid sequence of the new splice variant of the human P2X7-receptor
SEQ ID No. 3 nucleotide sequence cDNA of the wild type of the P2X7 receptor
SEQ ID No. 4 nucleotide sequence cDNA of the lacking 267 nucleotides ("gap")
SEQ ID No. 5 amino acid sequence of the wild type of the human P2X7 receptor
SEQ ID No. 6 P2X7—forward primer
SEQ ID No. 7 P2X7—backward primer
SEQ ID No. 8 GADPH—forward primer
SEQ ID No. 9 GADPH—backward primer
SEQ ID No. 10 TBP—forward primer
SEQ ID No. 11 TBP—backward primer

What is claimed is:

1. A method for the detection of a splice variant of P2X7 receptor in a living being, comprising:
   (a) providing a biological sample originating from the living being, and
   (b) detecting mRNA having the sequence of SEQ ID NO: 1, encoding exons 1-6 and 9-13 of the P2X7 receptor gene, but not exons 7 and 8 of the P2X7 receptor gene, or a polypeptide encoded thereby having the sequence of SEQ ID NO: 2 in the biological sample.

2. The method according to claim 1, wherein the biological sample is examined for the presence or the absence of the mRNA.

3. The method according to claim 2, wherein the examining comprises isolating total cellular RNA from the biological sample.

4. The method according to claim 3, wherein the examining comprises digesting DNA in the isolated total cellular RNA from the biological sample.

5. The method according to claim 2, wherein the examining comprises producing cDNA from the mRNA and detecting the presence of cDNA having the sequence encoding exons 1-6 and 9-13 of the P2X7 receptor gene, but not exons 7 and 8 of the P2X7 receptor gene.

6. The method according to claim 5, wherein detecting the presence of the cDNA having the sequence encoding exons 1-6 and 9-13 of the P2X7 receptor gene, but not exons 7 and 8 of the P2X7 receptor gene is conducted by polymerase chain reaction (PCR).

7. The method according to claim 6, wherein primers for the PCR are selected from the group consisting of SEQ ID NO: 6, SEQ ID NO: 7, SEQ ID NO: 10 and SEQ ID NO: 11.

8. The method according to claim 2, wherein for the presence or the absence of the mRNA is determined by a Northern blot assay.

9. The method according to claim 1, wherein the biological sample is examined for the presence or the absence of the polypeptide.

10. The method according to claim 8, wherein the examining comprises identifying binding of a binding molecule that specifically binds to the polypeptide.

11. The method according to claim 8, wherein the binding molecule comprises an antibody or an aptamer.

* * * * *

UNITED STATES PATENT AND TRADEMARK OFFICE
CERTIFICATE OF CORRECTION

PATENT NO. : 11,058,777 B2
APPLICATION NO. : 15/982416
DATED : July 13, 2021
INVENTOR(S) : Jens Gesche Page 1 of 1

It is certified that error appears in the above-identified patent and that said Letters Patent is hereby corrected as shown below:

In the Specification

In Column 3, Line 12, delete "Lokus" and insert --Locus--.

In Column 3, Line 48, delete "(95%)" and insert --($\geq$95%)--.

In Column 6, Line 32, delete "serium," and insert --serum,--.

In Column 6, Line 34, delete "mycoplasms." and insert --mycoplasma.--.

In Column 6, Line 42, delete "(Machery" and insert --(Macherey--.

In Column 6, Line 48, delete "geneeAmp®" and insert --geneAmp®--.

In Column 6, Line 52, delete "cyclation" and insert --cyclization--.

In Column 7, Line 21, delete "Minikits" and insert --Mini Kit--.

In Column 8, Line 20, delete "comittee." and insert --committee.--.

In Column 8, Lines 65-66, delete "GeneBank" and insert --GenBank--.

In Column 8, Line 66, delete "geneom/transcriptom" and insert --genome/transcriptome--.

Signed and Sealed this
Twenty-third Day of November, 2021

Drew Hirshfeld
*Performing the Functions and Duties of the*
*Under Secretary of Commerce for Intellectual Property and*
*Director of the United States Patent and Trademark Office*